(12) United States Patent
Luciow et al.

(10) Patent No.: US 8,076,277 B2
(45) Date of Patent: Dec. 13, 2011

(54) ENVIRONMENTALLY RESPONSIBLE PERSONAL CLEANSING COMPOSITIONS WITH HIGH PERFORMANCE

(75) Inventors: Chris Luciow, Scottsdale, AZ (US); James J. Dalton, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 12/839,478

(22) Filed: Jul. 20, 2010

(65) Prior Publication Data

US 2010/0279908 A1    Nov. 4, 2010

Related U.S. Application Data

(62) Division of application No. 12/150,221, filed on Apr. 25, 2008, now Pat. No. 7,981,851.

(51) Int. Cl.
*A61K 7/50* (2006.01)

(52) U.S. Cl. ........ 510/130; 510/156; 510/424; 510/426; 510/428; 510/475

(58) Field of Classification Search ......................... None
See application file for complete search history.

(56) References Cited

U.S. PATENT DOCUMENTS

| 5,573,756 | A | 11/1996 | Lambrechts |
| 6,358,516 | B1 | 3/2002 | Harod |
| 6,973,362 | B2 | 12/2005 | Long et al. |
| 7,096,084 | B2 | 8/2006 | Long et al. |
| 2005/0153852 | A1* | 7/2005 | Evans et al. .................. 510/130 |
| 2006/0029562 | A1 | 2/2006 | Lane et al. |

OTHER PUBLICATIONS

PCT International Search Report (PCT/US2009/039330) dated Nov. 8, 2009.

* cited by examiner

*Primary Examiner* — Necholus Ogden, Jr.
(74) *Attorney, Agent, or Firm* — David K. Benson

(57) ABSTRACT

A method is provided for formulating a personal cleansing composition. At least one primary surfactant, at least one secondary amphoteric and/or nonionic surfactant, at least one humectant, and at least one polymeric and/or quaternary conditioner are selected, each of these components having a natural and renewable resource origin. The primary and secondary surfactants are combined with the at least one humectant and the at least one conditioner in a final composition that includes the combined primary and secondary surfactants at less than about 14 wt. %, and includes the combined at least one humectant and at least one conditioner at less than 5.5 wt. %. After forming the final composition, an optimum performance index (OPI) is determined for the composition to ensure that the composition has an OPI of at least about 5.450. The OPI is calculated as: OPI=3÷((solids wt. %+Zein score)÷performance grade).

6 Claims, 3 Drawing Sheets

US 8,076,277 B2

ENVIRONMENTALLY RESPONSIBLE PERSONAL CLEANSING COMPOSITIONS WITH HIGH PERFORMANCE

CROSS-REFERENCE TO RELATED APPLICATIONS

This application is a Divisional of U.S. application Ser. No. 12/150,221, filed Apr. 25, 2008, now U.S. Pat. No. 7,981,851, herein incorporated by reference.

FIELD OF INVENTION

The present invention relates to various consumer, commercial, and industrial products, including but not limited to personal cleansing compositions. This invention more particularly relates to a variety of personal cleansing products, including body wash, liquid hand soaps, and natural body washes and hand soaps.

BACKGROUND

Many consumers have a preference for products that are purported to have lesser adverse environmental impacts than other similar products. This preference is evidenced by the growth of the "organic" foods market, and by the labeling of products with markings such as "environmentally friendly" or "green."

Apart from consumer preferences for environmentally friendly products, governments are increasingly regulating from an environmental standpoint the content of products. To ensure the widest distribution and acceptance of their products, manufacturers therefore have good reason to take into account a wide variety of differing environmental legal requirements.

The art has therefore begun to develop a number of different techniques for taking into account environmental issues when formulating products and acquiring their raw materials. In one approach the art has developed a public "grading system" that grades possible adverse environmental effects of products. Such systems are known to be associated with certain seals of approval by organizations having a perceived objective reputation regarding environmental matters.

To be commercially viable, a product should also meet certain cost and performance criteria, regardless of environmental attributes. Yet, available grading systems do not take into account a product's efficacy or the desirable attributes of a product. It is therefore desirable to provide a system for evaluating the environmental impact of chemical components, and thereby formulating products having improved environmental characteristics and performance attributes.

SUMMARY OF THE INVENTION

According to one exemplary embodiment of the invention, a personal cleansing composition is provided. The composition includes at least one primary surfactant having a natural and renewable resource origin, at least one secondary amphoteric and/or nonionic surfactant having a natural and renewable resource origin, at least one humectant having a natural and renewable resource origin, and at least one polymeric and/or quaternary conditioner having a natural and renewable resource origin. The composition has an optimum performance index (OPI) of at least about 5.450. The OPI is calculated by the formula: OPI=3÷((solids wt. %+Zein score)÷performance grade).

According to another exemplary embodiment of the invention, a method is provided for formulating a personal cleansing composition. To start, at least one primary surfactant, at least one secondary amphoteric and/or nonionic surfactant, at least one humectant, and at least one polymeric and/or quaternary conditioner are selected, each of these components having a natural and renewable resource origin. The primary and secondary surfactants are combined with the at least one humectant and the at least one conditioner in a final composition including the combined primary and secondary surfactants at less than about 14 wt. %, and further including the combined at least one humectant and at least one conditioner at less than 5.5 wt. %. After forming the final composition, an optimum performance index (OPI) is determined for the composition to ensure that the composition has an OPI of at least about 5.450, as calculated by the above formula.

DETAILED DESCRIPTION OF THE INVENTION

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and relative amounts of components described without departing from the scope of the invention as set forth in the appended claims. Additionally, though described herein largely in the context of a personal cleansing products, those skilled in the art will appreciate that the inventive concepts described herein may likewise apply to other products as well.

Three factors are considered with respect to the efficacy and environmental impact of the particular products of the present invention, namely, a) the use of biodegradable and low toxicity ingredients that include or are generated from renewable resources, b) low carbon dioxide emissions from the product itself, and c) the performance or efficacy of the product. Heretofore, compositions tended to be created by sacrificing at least one of the foregoing three factors when another was enhanced. The present invention minimizes or eliminates such sacrifice, realizing optimal benefits of each factor.

Figure 1:
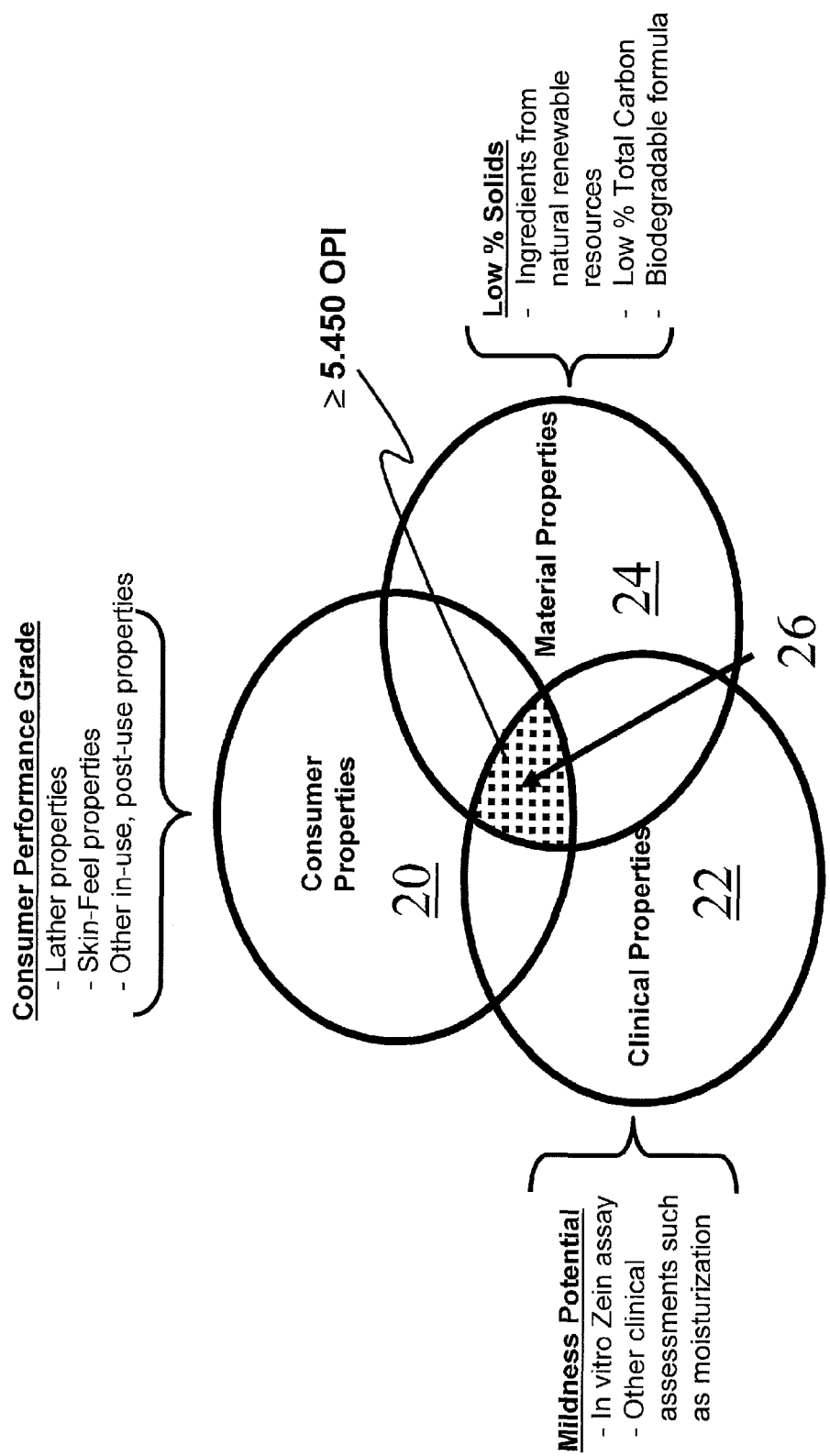
FIG. 1 is a chart that depicts the combination of selected consumer properties, clinical properties, and material properties to form an environmentally responsible cleansing composition.

According to various embodiments, the present invention accomplishes the goal of producing formulations for personal cleansing products that exhibit high consumer performance and are still environmentally responsible compositions. Referring to FIG. 1, a chart depicts the combination of selected consumer properties, clinical properties, and material properties to form an environmentally responsible cleansing composition according to an exemplary embodiment of the invention. As depicted in the chart, each of these property categories corresponds to a circular region, and the region in which all three property categories overlap corresponds to formulations for personal cleansing compositions that a) exhibit good performance attributes including high lather content during washing, pleasant skin-feel, and clean rinsing, b) have optimal mildness properties as determined by objective assays, and c) constitute environmentally responsible formulations that produce low carbon dioxide emissions and have high biodegradability. In addition, the cleansing compositions have an optimal performance score of at least 5.450, the formula for which will be hereinafter described.

Figure 2:
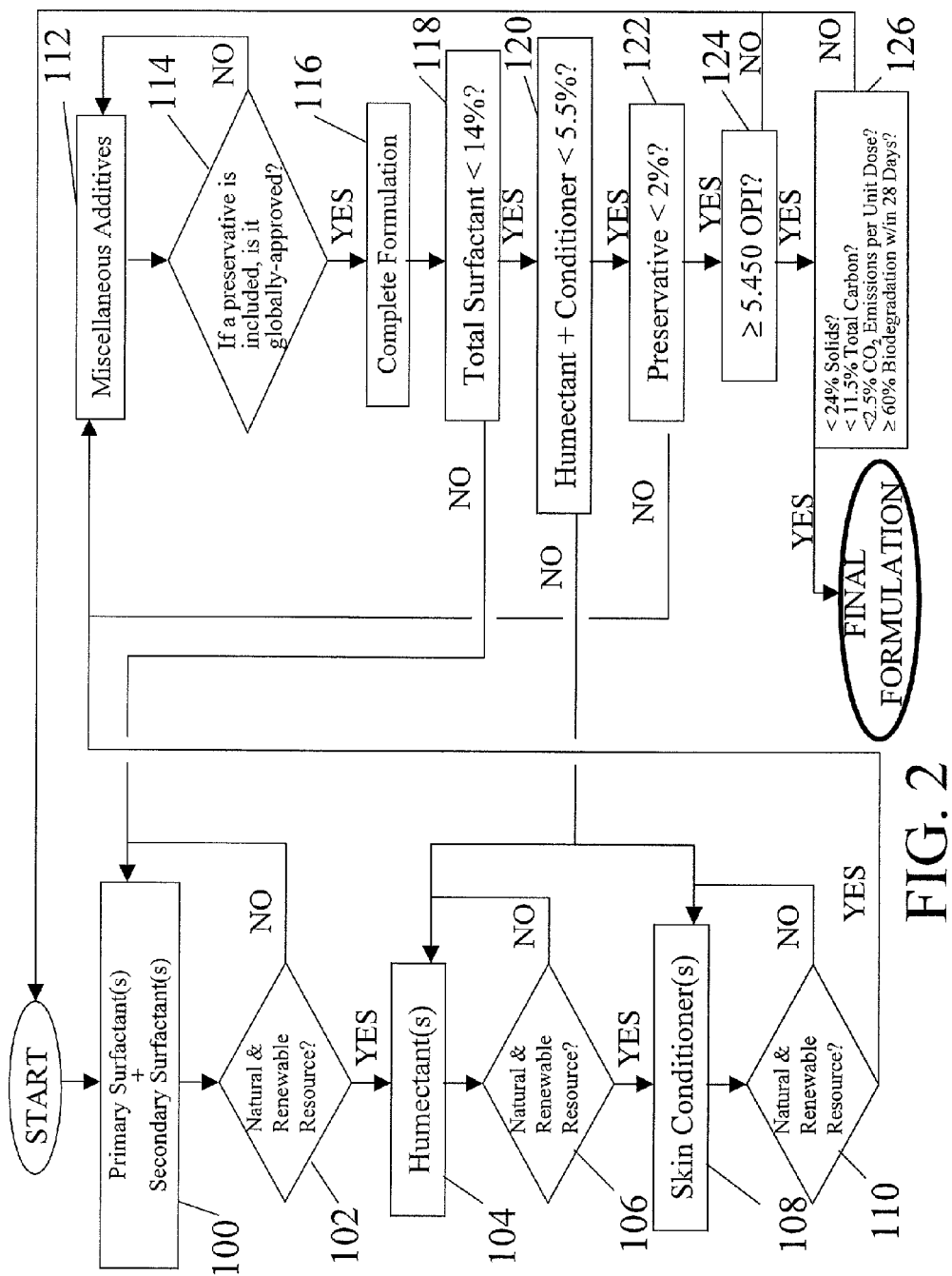
FIG. 2 is a flow diagram depicting a method of formulating an environmentally responsible cleansing composition.

FIG. 2 is a flow diagram depicting an exemplary method of formulating the environmentally responsible cleansing compositions having the attributes outlined in FIG. 1. As depicted, the method starts by first choosing at least one primary surfactant and at least one secondary surfactant as step 100. The at least one primary surfactant may be selected from any of the known anionic, amphoteric, or non-ionic surfactants known or previously used in the art of aqueous surfactant, detergent and cleansing compositions. Suitable anionic surfactants include, but are not limited to, alkyl sulfates, alkyl ether sulfates, alkyl aryl sulfonates, alkyl succinates, alkyl sulfosuccinates, N-alkoyl sarcosinates, alkyl phosphates, alkyl ether phosphates, alkyl ether carboxylates, alkylamino acids, alkyl peptides, alkoyl taurates, fatty acids, acyl and alkyl glutamates, and alkyl isethionates, most typically incorporated as their sodium, potassium, magnesium, ammonium and/or mono-, di- and triethanolammonium salts. The alkyl groups that make up the hydrophobic portion of these surfactants generally contain from 8 to 18 carbon atoms and may have various degrees of unsaturation. The alkyl ether sulfates, alkyl ether phosphates and alkyl ether carboxylates may contain from 1 to 10 ethylene oxide and/or propylene oxide units per molecule, and preferably contain 0 to 2 ethylene oxide units per molecule. Examples of suitable anionic surfactants include sodium and ammonium lauryl ether sulfate with 1-3 moles of ethylene oxide, sodium, ammonium, and triethanol-ammonium lauryl sulfate, disodium laureth sulfosuccinate, sodium cocoyl isethionate, sodium laureth-6 carboxylate, sodium $C_{12}$-$C_{15}$ pareth sulfate, sodium methyl cocoyl taurate, sodium cocoyl sarcosinate, and fatty acid soaps (sodium, potassium, magnesium, ammonium, and/or mono-, di-, or triethanol-ammonium salts of fatty acids). Suitable amphoteric and zwitterionic surfactant materials include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include cocamidopropyl betaine, sodium cocoamphoacetate, cocamidopropyl hydroxysultaine, and sodium cocamphopropionate. Suitable nonionic surfactants include but are not limited to aliphatic ($C_6$-$C_{18}$) primary or secondary linear or branched chain acids, alcohols or phenols, and alkyl phenol alkoxylates. Other suitable nonionics include mono- or di-alkyl alkanolamides and alkyl polysaccharides, and sorbitan fatty acid esters. Examples of suitable nonionic surfactants include coconut mono- or diethanolamide, coconut diglucoside, alkyl polyglucosides, cocamidopropyl and lauramine N-oxide, cetearyl alcohol, lanolin alcohol, stearic acid, and glyceryl stearate.

The at least one secondary surfactant ingredient is selected from known amphoteric/zwitterionic or non-ionic surfactant ingredients. Suitable amphoteric and zwitterionic surfactant materials include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to carbon atoms. Examples include cocamidopropyl betaine, sodium cocoamphoacetate, cocamidopropyl hydroxysultaine, and sodium cocamphopropionate. Suitable nonionic surfactants include but are not limited to aliphatic ($C_6$-$C_{18}$) primary or secondary linear or branched chain acids, alcohols or phenols. Other suitable nonionics include mono- or di-alkyl alkanolamides and alkyl polysaccharides, and sorbitan fatty acid esters. Examples of suitable nonionic surfactants include coconut mono- or diethanolamide, coconut diglucoside, alkyl polyglucosides, cocamidopropyl and lauramine N-oxide, cetearyl alcohol, lanolin alcohol, stearic acid, and glyceryl stearate.

Before continuing past the step of selecting primary and secondary surfactant ingredients, a determination is made regarding the origin of the selected surfactants as step 102. If each of the surfactants is determined to have a natural and renewable resource origin, then additional ingredients may be selected. If one or more of the primary and secondary surfactants do not have a natural and renewable resource origin, then those surfactants are not used, and, returning to step 100, different surfactants are selected. Natural and renewable resource origin chemicals are chemicals that have a starting source from a material that can be easily renewed or replaced, such as plants and animal products. Examples of renewable origin or resources include, but are not limited to, coconut oil, palm oil, corn, cotton, or wood. Examples of non-renewable resource origin chemicals or resources that cannot be easily replaced include, but are not limited to coal, petroleum, and silica or other mined minerals.

Continuing with the method, at least one humectant is selected as step 104. Humectants are moisture retentive materials, or "moisturizers." Suitable humectants include any hygroscopic material that is effective in providing moisturization to keratinized tissue such as skin and hair. Humectants suitable for use in the compositions of the present invention include any hygroscopic material having a solubility of at least 50% by weight in water at 25° C. Many of these preferred humectants will have one or more hydroxyl groups attached and are commonly classed as polyols, charbohydrates, amides, alkanolamides, or amines. Non-limiting examples of which include glycerin, sorbitol, honey, glucose, fructose, sucrose, lactic acid, sodium lactate, lactamide, sodium PCA, hydrogenated starch hydrosalate, hydrolyzed corn starch, lactamide MEA, and urea.

Before continuing past the step of selecting one or more humectant ingredients, a determination is made regarding the origin of the selected humectants as step 106. If each of the humectants is determined to have a natural and renewable resource origin, then additional ingredients for the formulation may be selected. If one or more of the humectants do not have a natural and renewable resource origin, then those humectants are not used, and, returning to step 104, one or more different humectants are selected.

Continuing further with the method of formulating a personal cleansing composition, at least one polymeric and/or quaternary skin conditioner is selected as step 108. Cationic quaternary ammonium compounds exhibit a positive charge that makes the material substantive to the slightly negatively charged skin and hair proteins, making most monomeric and polymeric quaternary molecules suitable for hair and skin conditioning purposes and as antistatics. Suitable cationic skin conditioning ingredients include a synthetic, but naturally derived cationic polymer, not limited to polyquaternium-10 or hydroxypropyl guar hydroxypropyltrimonium chloride or a quaternary ammonium compound, not limited to cocamidopropyl PG-dimonium chloride, hydrogenated starch hydrolysate hydroxypropyltrimonium chloride, hydroxypropyltrimonium hydrolyzed wheat protein, and the like.

Before continuing past the step of selecting one or more conditioners, a determination is made regarding the origin of the selected conditioners as step 110. If each of the conditioners is determined to have a natural and renewable resource origin, then additional ingredients for the formulation may be selected. If one or more of the conditioners do not have a natural and renewable resource origin, then those conditioners are not used, and returning to step 108, one or more different conditioners are selected.

After selecting surfactants, humectants, and skin conditioners, the method continues by selecting miscellaneous functional additives as step 112. Such additives may include pH and viscosity modifiers, fragrance oil, botanical extracts or oils, opacifying agents, and/or exfoliating agents. A few non-limiting examples of pH modifiers include citric acid, malic acid, salicylic acid, and sodium hydroxide. Sodium chloride and ammonium chloride are just a couple of non-limiting examples of viscosity modifiers. Several non-limiting examples of botanical extracts or botanical oils include *citrus grandis* (grapefruit) fruit extract, *punica granatum* Extract (pomegranate), *rosemary officinalis* (rosemary) leaf extract, *mentha peperita* (peppermint) leaf extract, *prunus amygdalus dulcis* (sweet almond) seed extract, almond oil, *theobroma cacao* (cocoa) seed butter, sunflowerseed oil, soybean oil, and lavender oil (*lavandula angustifolia*). A few non-limiting examples of opacifying agents include glycol stearate, glycol distearate, titanium dioxide, mica, and magnesium aluminum silicate. Finally, a few non-limiting examples of exfoliating agents include apricot seed meal, walnut shells, jojoba esters, silica, ground vanilla seeds, rice bran wax, and carnauba wax.

At least one preservative may also be included in the composition as part of the miscellaneous additives. If so, the method continues to step 114 for a determination of whether each preservative is further characterized as being globally approved, and being a non-formaldehyde or formaldehyde-releasing compound, and also being non-paraben and non-isothiazolinone in nature. If not, returning to step 112, different preservatives are selected as part of the miscellaneous additives. Non-limiting examples of suitable preservatives include benzoic acid, sorbic acid, sodium benzoate, sorbic acid, sodium salicylate, salicylic acid, phenoxyethanol, caprylyl glycol, tropolone, glucose oxidase, lactoperoxidase, and combinations of the like, intended for preservation of the finished formula; salts, opacifying agents, pH adjusters and or fragrance oils.

Having selected main ingredients and any other additive functional ingredients for the personal cleansing composition, the method continues to step 116 by completing the formulation. Next, decisions are made regarding whether groups of the main functional ingredients are included at suitable concentrations. As part of these decisions, it is determined as step 118 whether the total surfactant concentration is less than about 14 wt. %. If not, the method returns to step 100 for selection of the primary surfactants and/or the amount of each to be included. According to a preferred embodiment, the total concentration of the at least one primary surfactant ranges between about 3 and about 8 wt. %, and the total concentration of the at least one secondary surfactant ranges between about 2 and about 6 wt. %.

It is also determined as step 120 whether the combined humectant and skin conditioner concentrations is less than about 5.5 wt. %. If not, the method returns to steps 104 and/or 108 for selection of the humectant and/or the skin conditioner and/or the amount of each to be included. According to a preferred embodiment, the at least one humectant is included in the range of about 1 to about 4 wt. %, and the at least one conditioner is included in the range of about 0.1 to about 1.5 wt. %.

It is further determined as step 122 whether there is less than about 2 wt. % preservative in the completed formulation. If not, then the method returns to step 112 for selection of the preservative as part of the miscellaneous functional additives and/or the amount of preservative to be included. A preferred personal cleansing composition includes combined miscellaneous functional additives in the range of 0.1 to 2.0% by weight.

Continuing with the method, a determination is next made as step 124 regarding whether the personal cleansing composition has an optimum performance index (OPI) of at least about 5.450. The OPI is calculated by the formula:

$$OPI=3 \div [(solids\ wt.\ \% + Zein\ score) \div performance\ grade].$$

In order to obtain an adequate OPI, the percentage by weight of the total solids content is an important factor since lower amounts of solids impart to the personal cleansing composition a better environmental impact to the waste stream. An exemplary formulation has a total solids concentration that is no greater than about 24 wt. %.

Likewise, the Zein score for a personal cleansing composition is important because a low Zein score corresponds to a high prediction for skin mildness. Performing a test that measures the amount of corn protein (zein) that is dissolved by a surfactant mixture or cleansing product, such as a body wash, obtains the Zein score. The greater the amount of zein that is dissolved in a personal cleansing product, the harsher a product is indicated to be. Therefore, a low Zein score indicates a mild overall formulation, and consequently, a better product for personal cleansing use.

Finally, the performance grade is obtained by testing the personal cleansing composition for consumer overall liking. According to the OPI calculation, the performance grade is a number between 1 and 100, and equals a percentage of a maximum possible grade that can be awarded. For example, a preferred personal cleansing composition has a performance grade that is at least about 80% of a maximum possible grade for a consumer liking test. Particulars of such tests will be subsequently discussed.

Before returning to a discussion of the manner by which the total solids wt. %, the Zein score, and the performance grade for a personal cleansing composition contributes to the OPI, Table 1 below outlines three exemplary compositions ("Formulas A, C, and G"), including their main functional ingredients, that satisfy the previously-discussed composition qualifications, including their ingredients.

TABLE 1

| | Renewable Resource Origin | Formula A % by Weight | Formula C % by Weight | Formula G % by Weight |
|---|---|---|---|---|
| Water | Water | Q.S. | Q.S. | Q.S. |
| Polyquaternium-10 | Cotton | 0.2-0.5 | 0.1-0.4 | * |
| Glycerin (99%) | Coconut, Palm Oil or Tallow | 2.0-4.0 | 1.0-2.75 | 2.0-4.0 |
| Cocamidopropyl Betaine | Coconut Oil | 4.5-6.5 | 4.0-6.0 | 6.0-8.0 |
| PEG-7 Glyceryl Cocoate | Coconut Oil | 0.1-0.6 | 0.1-0.6 | * |
| Sodium Laureth Sulfate, 2 mole | Coconut or Palm Oil | 5.0-8.0 | 4.5-6.5 | |
| Decyl Glucoside | Corn | * | 0.75-2.0 | 3.0-5.0 |
| Sodium Lauroyl Lactylate | Corn | * | * | 0.5-1.25 |
| Cocamidopropyl Hydroxysultaine | Coconut Oil | 0.75-3.0 | * | |

TABLE 1-continued

| | Renewable Resource Origin | Formula A % by Weight | Formula C % by Weight | Formula G % by Weight |
|---|---|---|---|---|
| Sodium Cocoamphoacetate | Coconut Oil | * | * | 4.0-6.5 |
| Sodium Lauroyl Sarcosinate | Coconut or Palm Oil | * | * | 0.5-2.0 |
| PPG-2 Hydroxyethyl Coco/Isostearamide | * | 0.1-1.0 | * | 0.1-1.0 |
| Glycol Distearate | * | 0.5-1.0 | * | * |
| Cocamidopropyl PG-Dimonium Chloride | Coconut Oil | 0.1-0.75 | 0.1-0.75 | * |
| Coco-Glucoside, Glyceryl Oleate | Corn | * | * | 0.5-2.0 |
| Sodium Benzoate | * | 0.1-0.8 | 0.1-0.8 | 0.1-0.8 |
| Citric Acid, Anhydrous | Corn | 0.05-0.3 | 0.05-0.3 | 0.05-0.3 |
| Botanical Extracts | Plant | 0.05-0.2 | 0.05-0.2 | 0.05-0.2 |
| Sodium Chloride | * | 0.1-0.5 | 0.1-0.5 | * |
| Fragrance | * | 0.5-1.5 | 0.5-1.5 | 0.5-1.5 |

As previously discussed, the percentage by weight of the total solids content is one factor when calculating the OPI for a particular personal cleansing composition, and an exemplary formulation has a total solids concentration that is no greater than about 24 wt. %. Table 2 lists all of the ingredients for Formula A, and an example of a conventional commercialized formulation ("Comparative Formula B") is also included in the table.

TABLE 2

| | Formula A | Comparative Formula B |
|---|---|---|
| Formula Ingredients = | Water, Sodium Laureth Sulfate, Cocamidopropyl Betaine, Glycerin, Cocamidopropyl Hydroxysultaine, Fragrance, Hydrolyzed Yogurt Protein, *Aloe Barbadensis* Leaf Juice, Decyl Glucoside, PPG-2 Hydroxyethyl Coco/Isostearamide, PEG-7 Glyceryl Cocoate, Cocamidopropyl PG-Dimonium Chloride, Polyquaternium-10, Tetrasodium EDTA, Sodium Benzoate, Citric Acid, Sodium Chloride | Water, Glycine Soja Oil (Soybean) (or) *Helianthus Annuus* Seed Oil (Sunflower), Glycerin, Ammonium Lauryl Sulfate, Cocamidopropyl Betaine, Petrolatum, Ammonium Laureth Sulfate, Cocamide MEA, Lauric Acid, Fragrance, *Cucumis Sativus* Fruit Extract (Cucumber), *Camellia Sinensis* Leaf Extract (Green Tea), Guar Hydroxypropyltrimonium Chloride, Lanolin Alcohol, PEG-5 Cocamide, Propylene Glycol, DMDM Hydantoin, Citric Acid, Tetrasodium EDTA, Etidronic Acid, Green 3 (CI 42053), Titanium Dioxide (CI 77891), Yellow 10 (CI 47005) |
| Total Solids (%) = | 22.5 | 44.3 |

Before continuing with other factors that contribute to a personal cleansing composition's OPI, it is also preferable for a composition to produce low carbon dioxide emissions. Preliminarily, "carbon dioxide emissions" generally refers to a measure of the amount of carbon dioxide or $CO_2$ emitted through the combustion of fossil fuels; in the case of an organization, business or enterprise, as part of their everyday operations; in the case of an individual or household, as part of their daily lives; or in the case of a product or commodity, as part of reaching market. In terms of materials, it is essentially a measure of embodied energy, the result of life cycle analysis. This is directly related to the amount of natural resources consumed, increasingly used or referred to as a measure of environmental impact. Carbon dioxide is recognized as a greenhouse gas, of which increasing levels in the atmosphere are linked to global warming and climate change.

There are many versions of calculators available for carbon dioxide emissions. However, in simple terms, it can be measured by determining the total carbon in a given formulation and determining the amount of carbon dioxide the product will produce over time as it enters the waste stream.

For example, in the context of skin care positioned body washes, various known formulations have measurable $CO_2$ emissions assuming a 5.0 g typical dose/use level. An exemplary skin care or other personal cleansing composition has a total carbon percentage no greater than about 11.5%. Furthermore, an exemplary personal cleansing composition has carbon dioxide emissions that do not exceed 2.5 g per 5 g of product dose or usage. Table A lists the total carbon percentage, together with the carbon dioxide emissions for previously disclosed Formula A and Comparative Formula B.

TABLE 3

Skin Care Body Wash Comparison

| | Formula A | Comparative Formula B |
|---|---|---|
| Total Carbon (%) = | 7.8 | 27.2 |
| Grams CO2 emissions per single product dose/use = | 2.07 | 4.98 |
| Pounds CO2 emissions per 1,000 doses/uses = | 4.56 | 10.99 |

As another example, in the context of environmentally responsible body washes, various known formulations have measurable $CO_2$ emissions assuming a 5.0 g typical dose/use level. Table 4 lists the ingredients for Formula C, and Comparative Formulas D and E, along with their total solids content, their total carbon content, and their carbon dioxide emissions. The examples of Tables 3 and 4 illustrate exemplary carbon dioxide emissions by assuming that every component of the composition (all of the carbon) will break down and form $CO_2$.

TABLE 4

Natural Body Wash Carbon Comparison

| | Formula C | Comparative Formula D | Comparative Formula E |
|---|---|---|---|
| Formula Ingredients = | Water, Sodium Laureth Sulfate, Cocamidopropyl Betaine, Glycerin, Decyl Glucoside, Fragrance, PEG-7 Glyceryl Cocoate, Polyquaternium-10, Cocamidopropyl PG-Dimonium Chloride, Sodium Benzoate, Citric Acid, Sodium Chloride. | Water, Decyl Glucoside, Lauryl Glucoside, Coco-Betaine, Sodium Cocoyl Hydrolyzed Soy Protein, Sucrose Cocoate, Coco-Glucoside, Glyceryl Oleate, Honey, Betaine, Glycerin, Hydroxypropyl-trimonium Oligosaccharide, Natural Oils, Glucose Oxidase, Lacoperoxidase. | Water, Potassium Cocoate, Potassium Palmate, Glycerin, Coco-Glucoside, Sodium Chloride, Sucrose Cocoate, Lavender Oil and other Natural Oils, Hydrolyzed Wheat Protein, Hydrolyzed Wheat Gluten, Potassium Phytate |

TABLE 4-continued

Natural Body Wash Carbon Comparison

|  | Formula C | Comparative Formula D | Comparative Formula E |
|---|---|---|---|
| Total Solids (%) = | 20.0 | 31.1 | 37.8 |
| Total Carbon (%) = | 11.2 | 18.0 | 21.6 |
| Grams CO2 emissions per single product dose/use = | 2.05 | 3.30 | 3.96 |
| Pounds CO2 emissions per 1,000 doses/uses = | 4.52 | 7.27 | 8.72 |

Returning now with a discussion of factors that affect the calculation of a personal cleansing compositions's OPI, the Zein score for a personal cleansing composition is important because, as previously discussed, a low Zein score indicates a mild overall formulation, and consequently, a better product for personal cleansing use. An optimum range for a Zein score is 0% to 25%. One exemplary method for obtaining a Zein score includes preparing a 20 wt. % solution of the personal cleansing composition in water, and to add 1.5 g of zein powder into 30 g of the solution. After filtering and drying the solution, the amount of remaining zein is measured, and the percentage of zein that was dissolved in the personal cleansing composition is then calculated. The percentage is the number used to calculate the composition's OPI.

Table 5 lists the Zein scores for exemplary Formulas A and C, along with scores for conventional comparative formulas B, D, E, and F, based on in-vitro mildness tests.

TABLE 5

Zein Test (In-Vitro Mildness Test) of Various Body Washes

|  | Zein Score |
|---|---|
| Formula C | 21 |
| Formula A | 23 |
| Comparative Formula D | 4 |
| Comparative Formula F | 75 |
| Comparative Formula B | 52 |
| Comparative Formula E | 97 |

As previously discussed, the performance grade is the final variable that is used to calculate a personal cleansing composition's OPI, and is obtained by testing the personal cleansing composition for consumer overall liking. The performance grade is a number between 1 and 100, and is preferably is at least 80, meaning that a personal cleansing composition has a performance grade that is at least about 80% of a maximum possible grade for a consumer liking test. An exemplary method of screening the finished personal cleansing composition to gauge "performance" is a consumer liking test, such as a home use test, during which the consumer evaluates their overall liking for the composition, as well as their liking of key performance attributes. The test is performed blindly, meaning that the consumer is unable to determine from any containers, indicia, etc. the source of the composition. Further, the test is performed by a diverse pool of consumers covering a wide demographic range in categories that include, as appropriate, geography, race, age, and sex. A large number of consumers, i.e. preferably at least 200, test the composition, and a statistically significant difference should result at the 95% confidence level.

Personal cleansing compositions, selected and manufactured in accordance with various embodiments of the present invention, exhibit surprising consumer performance attributes, clinical moisturization, and in-vitro mildness results. Furthermore, as listed in Tables 6 and 7, the overall liking for exemplary skin care and natural body washes such as Formula A are significantly higher (83%) than that of comparative body washes such as Comparative Formula B (76.7%). For the data represented in Tables 6 and 7, the consumers were able to grade the compositions based on a nine-point scale, with 9.0 being the highest possible performance score, 7.0-9.0 being considered by the consumer as having high performance, 6.0-6.9 being considered by the consumer as having mediocre performance, and less than 6.0 being considered by the consumer as having inferior performance.

TABLE 6

Consumer Test Results for Skin Care Body Washes

|  | Formula A | Comparative Formula B |
|---|---|---|
|  | Base: Females 25-49 yrs old, users of skin-care body wash | |
|  | (218) A | (176) B |
| Liking/Agree scales (9-point) (9 Like/Agree Extremely- 1 Dislike/Disagree Extremely) | | |
| Overall Liking | 7.5B | 6.9 |
| Overall Liking, % of 9 Point Scale | 83.3 B | 76.7 |
| Overall Lather Liking | 7.9B | 6.6 |
| Skin Feels Smooth | 7.3B | 6.9 |
| I don't need to use much to get a good lather | 7.8B | 6.5 |
| Skin feels hydrated | 7.5B | 6.9 |

*A letter next to the number indicates a statistically higher significance at the 95% confidence level than the corresponding letter (product).

TABLE 7

Consumer Test Results for Natural Body Washes

|  | Formula C | Comparative Formula D | Comparative Formula E |
|---|---|---|---|
|  | Base: Females 24-59 yrs old, users of natural body wash | | |
|  | (236) | (236) | (234) |
| Liking scales (9-point) (9 Like Extremely- 1 Dislike Extremely) | | | |
| Overall Liking | 7.5 DE | 5.6 | 6.0 |
| Overall Liking, % of 9 Point Scale | 83.3 DE | 62.2 | 66.7 |
| Overall Fragrance Liking | 7.3 DE | 4.4 | 5.7 |
| Overall Strength of Fragrance Liking | 7.1 DE | 4.7 | 5.9 |
| Overall Lather Liking | 7.5 DE | 6.5 | 6.4 |
| Overall Appearance Liking | 7.3 DE | 5.7 | 6.2 |
| Overall Liking Way Made Skin Feel | 7.4 DE | 6.1 | 6.3 |
| Agreement Ratings (9-point) (1-completely disagree ▶ 9-completely agree) | | | |

TABLE 7-continued

Consumer Test Results for Natural Body Washes

| | Formula C | Comparative Formula D | Comparative Formula E |
|---|---|---|---|
| | Base: Females 24-59 yrs old, users of natural body wash | | |
| | (236) | (236) | (234) |
| Leaves skin feeling clean | 7.8 DE | 6.7 | 6.9 |
| Gently cleanses skin | 7.8 DE | 6.5 | 6.9 |
| Does not dry out skin | 7.6 DE | 6.2 | 6.6 |
| Leaves skin feeling moisturized | 7.1 DE | 5.5 | 6.0 |
| Leaves skin feeling soft and smooth | 7.3 DE | 6.0 | 6.3 |

The combination of the three variables, total solids, Zein score, and the performance grade, produces an OPI of greater than 5.450 for personal cleansing compositions of the present invention. Table 8 lists the OPI for exemplary formulas A and C, and also for commercialized Comparative Formulas B, D, E, and F.

TABLE F

OPI of Various Body Washes

| Formula | % Solids | Zein Mildness Score | Consumer Overall Liking % of 9 pt Scale | OPI |
|---|---|---|---|---|
| Formula C | 20.0 | 21 | 83.3 | 6.095 |
| Formula A | 22.5 | 23 | 83.3 | 5.492 |
| Comparative Formula D | 31.1 | 4 | 62.2 | 5.316 |
| Comparative Formula F | 14.9 | 75 | 80.0 | 2.670 |
| Comparative Formula B | 44.3 | 52 | 76.7 | 2.389 |
| Comparative Formula E | 37.8 | 97 | 66.7 | 1.484 |

Figure 3:
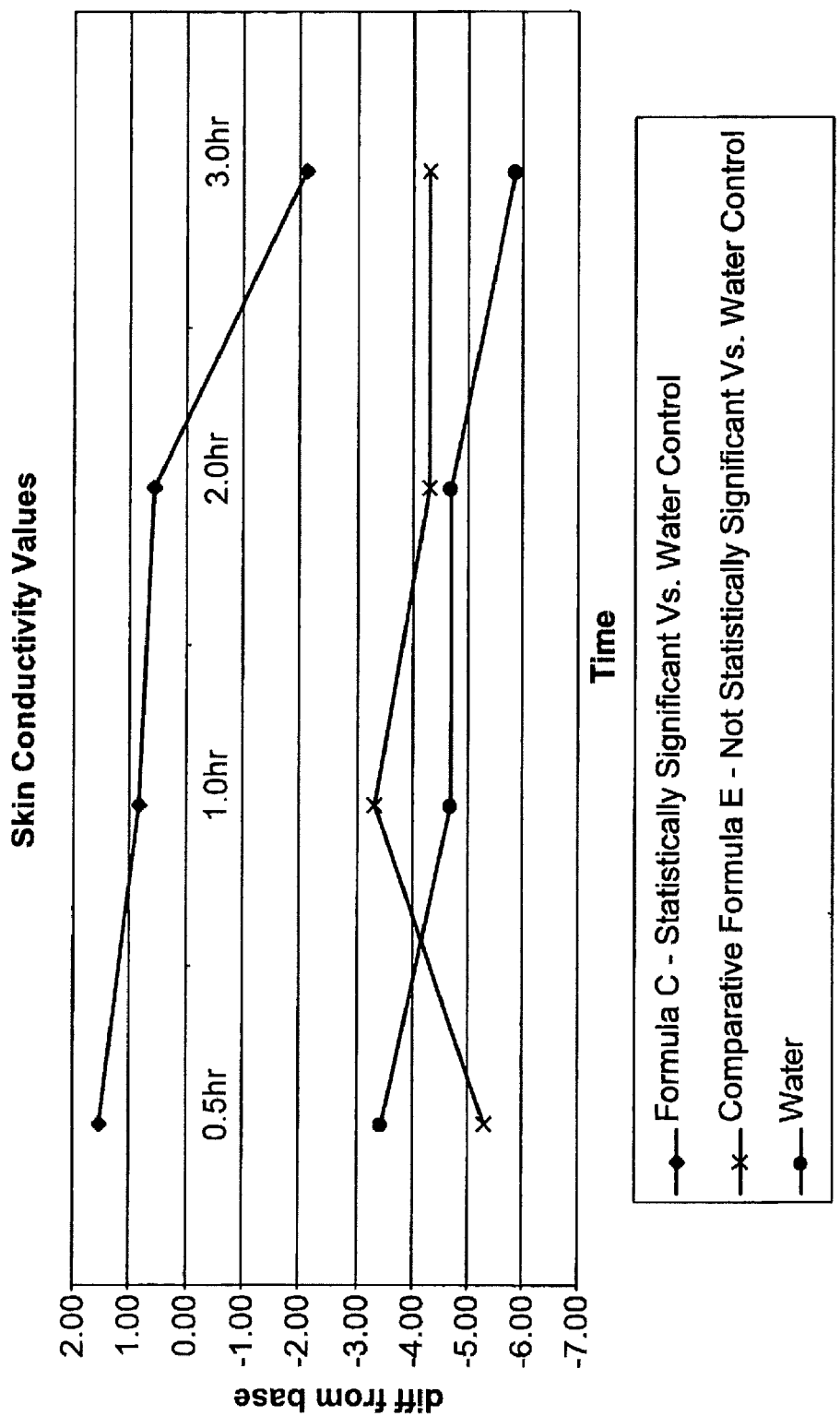
FIG. 3 is a graph that compares skin conductivity values after washing with various personal cleansing compositions, and compares these values with skin rinsed solely with water.

The personal cleansing compositions may be further optimized in terms of their environmental, skin or hair mildness, or consumer liking performance. For example, an exemplary composition imparts superior skin moisturization when compared with water. As one example, FIG. 3 is a graph that compares skin conductivity values after washing with Formula C and Comparative Formula E, and compares these values with skin rinsed solely with water, with all testing being performed following the standard leg controlled application test (LCAT). According to an exemplary LCAT method, subjects are washed with an adequate amount (i.e. 250 ml) of a cleansing composition after obtaining baseline conductivity measurements for the skin prior to washing. Visual and instrumental measurements are then taken at 30 minutes, 1 hour, 2 hours, and 3 hours after washing. A conductivity meter measures skin surface conductivity. Skin that contains a high level of moisture will exhibit higher conductance properties. Visual dryness is also measured to indicate how moisturized the skin appears. The top layer of the sratum corneum will appear smoother and/or less flaky for more moisturized skin. As depicted in the graph, cleaning with Formula C imparts significantly improved skin conductivity, and consequently significantly improved moisturization, to skin than cleaning with water alone, while Comparative Formula E is not significantly different than water alone.

Furthermore, exemplary personal cleansing compositions of the present invention also are formed from ingredients that are biodegradable. More particularly, preferable personal cleansing compositions include the at least one primary and secondary surfactants, and the at least one humectant as compounds that experience greater than 60% biodegradation within 28 days.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method of formulating a personal cleansing composition, comprising:
   selecting at least one primary surfactant;
   determining whether the at least one primary surfactant has a natural and renewable resource origin, and if it does not, then selecting instead at least one different primary surfactant that has a natural and renewable resource origin;
   selecting at least one secondary amphoteric and/or nonionic surfactant;
   determining whether the at least one secondary amphoteric and/or nonionic surfactant has a natural and renewable resource origin, and if it does not, then selecting instead at least one different secondary amphoteric and/or nonionic surfactant that has a natural and renewable resource origin;
   selecting at least one humectant;
   determining whether the at least one humectant has a natural and renewable resource origin, and if it does not, then selecting instead at least one different humectant that has a natural and renewable resource origin;
   selecting at least one polymeric and/or quaternary conditioner;
   determining whether the at least one polymeric and/or quaternary conditioner has a natural and renewable resource origin, and if it does not, then selecting instead at least one different polymeric and/or quaternary conditioner that has a natural and renewable resource origin;
   combining the selected primary and secondary surfactants with the at least one selected humectant and the at least one selected conditioner in a final composition including the combined primary and secondary surfactants at less than about 14 wt. %, and further including the combined at least one humectant and at least one conditioner at less than 5.5 wt. %;
   ensuring that the final composition has a total carbon percentage no greater than about 11.5%;

ensuring that the final composition has carbon dioxide emissions that do not exceed about 2.5 g per 5 g of product dose or usage; and ensuring that the final composition having an optimum performance index (OPI) of at least about 5.450, calculated by the formula:

OPI=3÷((solids wt. %+Zein score)÷performance grade).

2. The method according to claim 1, further comprising:
ensuring that the performance grade component of the OPI is at least about 80% of a maximum possible grade.

3. The method according to claim 1, further comprising:
ensuring that the solids wt. % component of the total solids concentration is no greater than about 24 wt. %.

4. The method according to claim 1, further comprising:
selecting a preservative that is a non-formaldehyde-releasing compound and also is a non-paraben and a non-isothiazolinone compound; and
combining the preservative as part of the final composition.

5. The method according to claim 1, further comprising:
ensuring that the final composition imparts superior skin moisturization when compared with water.

6. The method according to claim 1, wherein the step of selecting the at least one primary and secondary surfactants and the at least one humectant includes selecting compounds that experience greater than 60% biodegradation within 28 days.

* * * * *